(12) United States Patent
Cauda et al.

(10) Patent No.: US 12,742,707 B2
(45) Date of Patent: Sep. 22, 2026

(54) METHOD OF ACQUIRING LIQUID BIOLOGICAL SAMPLES FROM AN EXTRACORPOREAL CIRCUIT FOR AN EXTRACORPOREAL BLOOD PURIFICATION TREATMENT AND RELATED APPARATUS AND SYSTEM

(71) Applicants: POLITECNICO DI TORINO, Turin (IT); UNIVERSITÀ DEGLI STUDI DI FIRENZE, Florence (IT);

(Continued)

(72) Inventors: Valentina Cauda, Moncalieri (IT); Andrea Ancona, Turin (IT);

(Continued)

(73) Assignees: Politecnico Di Tornio, Turin (IT); Universita Degli Studi Firenze, Florence (IT); Azienda Ospedaliero Universitaria Di Careggi, Florence (IT); Azienda Ospedaliera Universitaria Meyer Irccs, Florence (IT)

(*) Notice: Subject to any disclaimer, the term of this patent is extended or adjusted under 35 U.S.C. 154(b) by 257 days.

(21) Appl. No.: 18/723,818

(22) PCT Filed: Dec. 15, 2022

(86) PCT No.: PCT/IB2022/062318

§ 371 (c)(1),
(2) Date: Jun. 24, 2024

(87) PCT Pub. No.: WO2023/119085

PCT Pub. Date: Jun. 29, 2023

(65) Prior Publication Data

US 2025/0060287 A1 Feb. 20, 2025

(30) Foreign Application Priority Data

Dec. 24, 2021 (IT) ........................ 102021000032621

(51) Int. Cl.
*G01N 1/20* (2006.01)
*G01N 1/10* (2006.01)
(Continued)

(52) U.S. Cl.
CPC ................. *G01N 1/20* (2013.01); *G01N 1/14* (2013.01); *G01N 33/491* (2013.01); *G01N 2001/1031* (2013.01); *G01N 2001/1418* (2013.01)

(58) Field of Classification Search
CPC .... G01N 33/49; G01N 33/86; G01N 33/4925; G01N 21/05; G01N 33/4905;
(Continued)

(56) References Cited

U.S. PATENT DOCUMENTS 9,562,914 B2 * 2/2017 Jain ........................ G16B 40/00
12,070,539 B2 * 8/2024 Rovatti ............... A61M 1/1656
(Continued)

FOREIGN PATENT DOCUMENTS

DE 101 49 809 C1 5/2003
EP 1 029 554 A2 8/2000
(Continued)

OTHER PUBLICATIONS

International Preliminary Report on Patentability dated Jun. 20, 2024, issued in PCT Application No. PCT/IB2022/062318, filed Dec. 15, 2022.

(Continued)

*Primary Examiner* — Andre J Allen
(74) *Attorney, Agent, or Firm* — Workman Nydegger; Dana Tangren

(57) ABSTRACT

A method of acquiring liquid biological samples from an extracorporeal circuit for subjecting a patient to an extracorporeal blood purification treatment includes a sampling phase wherein: I) a first sampling port is in fluidic commu- (Continued)

nication with a first collection chamber via a first hydraulic machine, the first sampling port being operatively connected to a first haematic line inputted to a haemodiafilter of the extracorporeal circuit; II) a second sampling port is in fluidic communication with a second collection chamber via a second hydraulic machine, the second sampling port being operatively connected to a second haematic line outputted from said haemodiafilter; III) a third sampling port is in fluidic communication with a third collection chamber via a third hydraulic machine, the third sampling port being operatively connected to an effluent line of the haemodiafilter, wherein each hydraulic machine fills a corresponding collection chamber with a corresponding biological sample.

9 Claims, 3 Drawing Sheets

(51) Int. Cl.
*G01N 1/14* (2006.01)
*G01N 33/49* (2006.01)

(58) Field of Classification Search
CPC ........... G01N 2021/3144; G01N 21/31; G01N 33/491; G01N 21/274; G01N 21/3151; G01N 21/3577; G01N 21/85; G01N 21/0303; G01N 2021/3148; G01N 21/59; G01N 33/6896; G01N 21/255; G01N 2800/52; G01N 2201/062; G01N 33/53; G01N 15/05; G01N 33/573; G01N 21/33; G01N 2291/02466; G01N 2021/3155; G01N 21/359; G01N 21/84; G01N 2021/036; G01N 21/251; G01N 2021/0364; G01N 2015/055; G01N 21/314; G01N 33/6893; G01N 33/721; G01N 2035/00495; G01N 21/278; G01N 2500/00; G01N 33/80; G01N 21/25; G01N 21/532; G01N 21/90; G01N 11/06; G01N 33/4915; G01N 2021/058; G01N 33/54313; G01N 21/80; G01N 2201/0621; G01N 33/48; G01N 15/01; G01N 19/00; G01N 21/276; G01N 2333/9645; G01N 33/56983; G01N 2015/1472; G01N 2021/6432; G01N 21/6428; G01N 21/645; G01N 2201/0646; G01N 27/902; G01N 27/904; G01N 2021/8405; G01N 21/53; G01N 27/06; G01N 27/3271; G01N 33/84; G01N 2015/012; G01N 2015/018; G01N 2015/084; G01N 2400/40; G01N 2800/226; G01N 2021/6482; G01N 2201/0627; G01N 27/07; G01N 21/51; G01N 27/327; G01N 27/3272; G01N 27/3277; G01N 15/0826; G01N 2015/1006; G01N 2021/3181; G01N 21/6408; G01N 21/7703; G01N 2201/0634; G01N 2201/0636; G01N 2201/12; G01N 2800/26; G01N 29/032; G01N 33/66; G01N 33/68; G01N 15/14; G01N 29/024; G01N 2021/7763; G01N 2030/8813; G01N 21/77; G01N 2201/0668; G01N 24/08; G01N 24/088; G01N 27/02; G01N 29/222; G01N 15/075; G01N 2800/2828; G01N 37/00; G01N 11/14; G01N 2015/0092; G01N 21/27; G01N 21/6402; G01N 2201/064;G01N 2291/02433; G01N 2333/59; G01N 27/04; G01N 29/02; G01N 29/223; G01N 33/569; G01N 35/1079; G01N 15/12; G01N 15/1429; G01N 15/1433; G01N 2015/1402; G01N 2021/0367; G01N 2021/6439; G01N 21/552; G01N 21/6456; G01N 2800/245; G01N 33/5088; G01N 33/538; G01N 33/6854; G01N 15/0211; G01N 15/0606; G01N 2021/0346; G01N 2021/3166; G01N 2021/646; G01N 2035/00306; G01N 2035/00316; G01N 2035/1032; G01N 2035/1062; G01N 21/78; G01N 2201/0407; G01N 2201/0476; G01N 2201/0618; G01N 2201/0626; G01N 2201/1288; G01N 2333/4725; G01N 33/497; G01N 33/50; G01N 33/56911; G01N 33/575; G01N 33/585; G01N 35/1095; G01N 1/4077; G01N 2021/0378; G01N 2021/6417; G01N 2021/7786; G01N 21/01; G01N 21/03; G01N 21/631; G01N 21/6486; G01N 2291/102; G01N 27/00; G01N 2800/50; G01N 33/48728; G01N 33/5002; G01N 33/5005; G01N 33/5064; G01N 11/162; G01N 15/131; G01N 15/1459; G01N 21/76; G01N 21/93; G01N 2201/0224; G01N 2201/0612; G01N 2201/065; G01N 2291/044; G01N 2333/96486; G01N 33/5091; G01N 35/00; G01N 35/00584; G01N 1/14; G01N 15/1484; G01N 2021/1736; G01N 21/49; G01N 2201/0662; G01N 27/26; G01N 33/48707; G01N 33/492; G01N 33/5094; G01N 35/0092; G01N 1/20; G01N 15/042; G01N 15/06; G01N 15/10; G01N 2001/1031; G01N 2001/1418; G01N 2001/4016; G01N 2001/4083; G01N 21/65; G01N 2201/1296; G01N 2291/02818; G01N 2333/4724; G01N 2333/8128; G01N 29/345; G01N 33/15; G01N 33/487; G01N 33/5011; G01N 33/548; G01N 35/10; G01N 15/1031; G01N 2021/177; G01N 2021/4153; G01N 21/07; G01N 21/4133; G01N 2333/4709; G01N 2333/96419; G01N 2440/18; G01N 27/48; G01N 2800/04; G01N 29/022; G01N 33/54346; G01N 33/6875; G01N 33/74; G01N 1/2035; G01N 11/167; G01N 2015/0846; G01N 2015/1486; G01N 21/8806; G01N 2291/02809; G01N 2333/165; G01N 2333/805; G01N 2500/10; G01N 27/403; G01N 2800/32; G01N 29/24; G01N 29/2418; G01N 29/343; G01N 33/4833; G01N 33/48778; G01N 33/5032; G01N 33/54326; G01N 1/286; G01N 11/16; G01N 15/1404; G01N 15/149; G01N 2001/2866; G01N 2015/016; G01N 2021/0112; G01N 2035/00158; G01N 21/35; G01N 2201/0624; G01N 2201/129; G01N 2203/0019; G01N 2291/02881; G01N 2291/048; G01N 2333/03; G01N 2333/135; G01N 2333/245; G01N 2333/31; G01N 2333/525; G01N 2333/535; G01N 2333/5406; G01N 2333/5412; G01N 2333/545; G01N 2333/75; G01N 2500/02; G01N 27/333; G01N 27/40; G01N 2800/2821; G01N 2800/347; G01N 2800/7095; G01N 29/4427; G01N 33/00; G01N 33/48735; G01N 33/48785; G01N 33/5008; G01N 33/5058; G01N 33/5308; G01N 33/543; G01N 33/555; G01N 33/559; G01N 33/56916; G01N 33/56938; G01N 33/582; G01N 33/6878; G01N 33/92; G01N 1/10; G01N 1/28; G01N 1/30; G01N 1/38; G01N 11/00; G01N 11/10; G01N 2015/047; G01N 2015/1488; G01N 2021/1738; G01N 2021/4709; G01N 2035/00881; G01N 21/47; G01N 21/8851; G01N 2203/0005; G01N 2203/005; G01N 2291/015; G01N 2291/02836; G01N 2333/47; G01N 2333/745; G01N 2333/96494; G01N 2400/50; G01N 27/08; G01N 27/221; G01N 27/4163; G01N 2800/22; G01N 2800/222; G01N 2800/60; G01N 29/348; G01N 3/38; G01N 30/02; G01N 33/483; G01N 33/5014; G01N 33/5438; G01N 33/54386; G01N 33/551; G01N 33/552; G01N 33/558; G01N 33/564; G01N 35/1009; G01N 1/34; G01N 1/42; G01N 1/44; G01N 11/02; G01N 13/00; G01N 13/04; G01N 15/1012; G01N 2001/2873; G01N 2015/1014; G01N 2015/1019; G01N 2021/6434; G01N 2021/6491; G01N 2021/656; G01N 2030/525; G01N 2030/567; G01N 2030/8822; G01N 2035/00326; G01N 2035/00544; G01N 2035/00702; G01N 2035/00821; G01N 21/39; G01N 21/55; G01N 21/62; G01N 21/63; G01N 21/64; G01N 2201/061; G01N 2201/0625; G01N 2201/069; G01N 2201/0691; G01N 2223/03; G01N 2223/1016; G01N 2223/401; G01N 2291/012; G01N 2291/02416; G01N 23/046; G01N 2333/4728; G01N 2333/475; G01N 2333/515; G01N 2333/70503; G01N 2333/70525; G01N 2333/70546; G01N 2333/7056; G01N 2333/70564; G01N 2333/71; G01N 2333/7452; G01N 2333/78; G01N 2333/902; G01N 2405/04; G01N 25/00; G01N 27/048; G01N 27/3274; G01N 27/3275; G01N 27/3335; G01N 27/404; G01N 2800/00; G01N 2800/044; G01N 2800/56; G01N 29/22; G01N 29/48; G01N 33/0067; G01N 33/4972; G01N 33/5044; G01N 33/5047; G01N 33/5302; G01N 33/545; G01N 33/57557; G01N 33/57585; G01N 33/577; G01N 33/723; G01N 35/00693; G01N 35/00732; G01N 35/0099; G01N 35/08; G01N 35/1011; G01N 9/002; G01N 9/36; G01N 15/00; G01N 15/082; G01N 15/1434; G01N 19/08; G01N 2009/026; G01N 2011/0026; G01N 2011/0066; G01N 2011/008; G01N 2011/147; G01N 2013/003; G01N 2021/0392; G01N 2021/052; G01N 2021/1765; G01N 2021/1772; G01N 2021/178; G01N 2021/3159; G01N 2021/4711; G01N 2021/6463; G01N 2030/002; G01N 2030/0045; G01N 2030/027; G01N 2030/322; G01N 2030/522; G01N 2030/562; G01N 2035/00237; G01N 2035/00346; G01N 2035/1034; G01N 21/17; G01N 21/3103; G01N 21/37; G01N 21/431; G01N 21/4785; G01N 21/534; G01N 21/5907; G01N 21/658; G01N 21/783; G01N 21/91; G01N 21/94; G01N 21/95; G01N 2201/06186; G01N 2201/0631; G01N 2201/0696; G01N 2201/1244; G01N 2203/0003; G01N 2203/0073; G01N 2203/0075; G01N 2203/0242; G01N 2203/0246; G01N 2203/0262; G01N 2203/0676; G01N 2203/0682; G01N 2223/076; G01N 2291/017; G01N 2291/022; G01N 2291/0224; G01N 2291/0258; G01N 23/223; G01N 2333/05; G01N 2333/44; G01N 2333/445; G01N 2333/45; G01N 2333/4737; G01N 2333/521; G01N 2333/523; G01N 2333/5421; G01N 2333/57; G01N 2333/8125; G01N 2333/90; G01N 2333/96436; G01N 2333/96463; G01N 2600/00; G01N 27/10; G01N 27/30; G01N 27/301; G01N 27/307; G01N 27/3273; G01N 27/3278; G01N 27/4035; G01N 27/4166; G01N 27/622; G01N 2800/02; G01N 2800/224; G01N 2800/323; G01N 2800/324; G01N 2800/368; G01N 29/00; G01N 29/036; G01N 29/04; G01N 29/14; G01N 29/228; G01N 29/28; G01N 29/44; G01N 29/46; G01N 3/02; G01N 3/08; G01N 3/32; G01N 30/06; G01N 30/56; G01N 30/6017; G01N 30/6052; G01N 30/606; G01N 33/0006; G01N 33/0078; G01N 33/4875; G01N 33/502; G01N 33/5041; G01N 33/5082; G01N 33/52; G01N 33/525; G01N 33/54353; G01N 33/54387; G01N 33/54393; G01N 33/553; G01N 33/56966; G01N 33/5759; G01N 33/58; G01N 33/6803; G01N 33/6863; G01N 33/6866; G01N 33/6884; G01N 33/689; G01N 33/72; G01N 33/726; G01N 33/94; G01N 33/96; G01N 35/02; G01N 35/085; G01N 35/1004; G01N 35/1097; G01N 7/16; G01N 9/02

See application file for complete search history.

(71) Applicants: AZIENDA OSPEDALIERO UNIVERSITARIA DI CAREGGI, Florence (IT); AZIENDA OSPEDALIERA UNIVERSITARIA MEYER IRCCS, Florence (IT)

(72) Inventors: Gianluca Villa, Vaglia (IT); Stefano Romagnoli, Florence (IT); Zaccaria Ricci, Rome (IT)

(56) References Cited

U.S. PATENT DOCUMENTS

| | | | | |
|---|---|---|---|---|
| 2018/0110916 | A1 | 4/2018 | Xue | |
| 2024/0399036 | A1* | 12/2024 | Maierhofer | A61M 1/1613 |

FOREIGN PATENT DOCUMENTS

| | | | |
|---|---|---|---|
| WO | 2012/127513 | A1 | 9/2012 |
| WO | 2021/127649 | A1 | 6/2021 |

OTHER PUBLICATIONS

International Search Report and Written Opinion dated Mar. 29, 2023, issued in PCT Application No. PCT/IB2022/062318, filed Dec. 15, 2022.

* cited by examiner

METHOD OF ACQUIRING LIQUID BIOLOGICAL SAMPLES FROM AN EXTRACORPOREAL CIRCUIT FOR AN EXTRACORPOREAL BLOOD PURIFICATION TREATMENT AND RELATED APPARATUS AND SYSTEM

BACKGROUND OF THE DISCLOSURE

1. The Field of the Disclosure

The present invention relates to a method of acquiring liquid biological samples from an extracorporeal circuit for subjecting a patient to an extracorporcal blood purification treatment. In particular, described herein are a method of acquiring liquid biological samples from an extracorporcal circuit for subjecting a patient to an extracorporeal blood purification treatment, an apparatus for acquisition of liquid biological samples, an apparatus for analysis of acquired liquid biological samples, and the corresponding system.

2. The Relevant Technology

The present invention can be used for monitoring one or more parameters of the patient and/or of the extracorporeal treatment administered to the patient, such as, for example, the haematic concentration of a solute, a delivered clearance value and/or a sieving coefficient value. The present invention can be used for extracorporeal blood purification treatments like, for example, haemodialysis (HD), haemofiltration (HF), hacmodiafiltration (HDF). In particular, the present invention can be used for intensive-care dialysis treatments, such as, for example, CRRT (Continuous Renal Replacement Therapy) treatments, CAVH (Continuous Artero Venous Haemofiltration) treatments, and CVVH (Continuous Veno Venous Haemofiltration) treatments, which are frequently used in intensive care settings to support kidney functions of patients suffering from acute renal damage. Such CRRT, CAVH and CVVH treatments subject a blood tissue of the patient to a continuous extracorporcal treatment by means of an extracorporcal blood purification machine. Similarly to the patient's physiological renal function, such treatments permit the elimination of waste solutes and substances through an artificial semipermeable haemodiafiltration membrane within a haemodiafilter of the extracorporeal circuit. Solutes can pass through such membrane by concentration difference (diffusive clearance), by pressure difference (convective clearance), and by direct adsorption.

The purification amount that is needed as a result of such dialysis treatments identifies the concept of purification dose. Just like a drug dose, which expresses posology, the purification dose defines, in dialysis treatments, a clearance amount to be obtained for a given solute. Clearance, i.c. the quantity of blood that is purified of a substance per time unit, is a solute-dependent concept which is mainly related to the capacity of the haemodiafiltration membrane to let itself be crossed by the solute, e.g. by concentration or pressure gradient. This phenomenon depends on the ratio between a molecular size of the solute and a pore size of the membrane; generally, the greater the size of the solute, the lower its capacity to pass through the pores of the haemodiafiltration membrane, and hence the lower the possibility for such solute to be eliminated from the patient's blood.

In particular, the capacity of the solute to go past the haemodiafiltration membrane, and to be then eliminated with waste fluids generated by the treatments, decreases dynamically and unpredictably during the treatment, so much so that the purification dose actually delivered to the patient, i.e. the clearance, turns out to be systematically different from the prescribed purification dosc. This phenomenon affects the removal of solutes as a function of their size, and is generally more marked for larger solutes, which encounter more difficulty in passing through the haemodiafiltration membrane. The reasons for such a transmembrane clearance reduction can be summarized into the concept known as membrane fouling, which is a stochastic process wherein multiple phenomena, including protein-membrane adhesion and local coagulation activation, significantly reduce the transmembrane passage of solutes that need be removed from the patient's blood tissue.

The resulting involuntary undertreatment may have adverse effects on the patient's clinical state, to such an extent that careful and frequent monitoring of the delivered clearance (i.e. the current effective delivered dose) is now strongly recommended by ADQI (Acute Dialysis Quality Initiative), i.e. the most authoritative international scientific society in this field.

The techniques currently known in the art for measuring the delivered clearance require at least one manual taking of samples of blood and waste liquids, also referred to as effluent, from predefined points of the extracorporeal circuit, following a specific procedure; moreover, such biological samples must be sent to a laboratory for quantifying the concentrations of the solute under examination, i.e. urea, which is conventionally chosen as a solute representative of uremic retention during acute kidney disease.

The techniques currently known in the art for measuring the delivered clearance suffer from a number of drawbacks, which will be illustrated below.

A first drawback is due to the fact that such techniques are extremely complex: as a matter of fact, a proper biological sampling procedure requires that three healthcare professionals mutually co-operate to manually take two blood samples and one effluent liquid sample from the extracorporcal circuit, e.g. by means of syringes. In such conditions, there is often a high biological risk for the healthcare professionals and also a high risk of sampling errors, which may invalidate the whole evaluation process. Furthermore, in intensive care settings, where spaces are small and personnel is lacking in number, it is often impossible to involve three different professionals in the sampling process.

A second drawback comes from the fact that a concentration value of the solute under examination is generally not available in real time, but approximately 4-6 hours after collection. In point of fact, the acquired biological samples must be sent, following non-standard operative procedures, to an analysis laboratory for quantifying the solute under examination. Such procedures are often lacking in correctly sending the request to the analysis laboratory, where confusion may arise due to the reception of several different biological samples and to the nature of the sample of effluent liquid, which is not comparable with either blood or urine. Consequently, further contact with the laboratory is often necessary to clarify the nature of the request, thus further protracting the response time and increasing the organizational engagement required of healthcare workers. This only permits a historical evaluation of the delivered clearance. It is however known that a dynamic correction of the prescribed purification dose, aimed at adjusting the extracorporeal clearance to the patient's actual metabolic needs, requires that the delivered clearance be monitored substantially in real time.

A further drawback is due to the fact that, since urea is considered to be the only solute to be evaluated for measuring the delivered clearance, the results thereby obtained can only be consistent with solutes having a molecular mass which is similar to that of urea, i.e. of the order of a few dalton. It is known, however, that the target of CRRT treatments in intensive care settings mainly consists of medium-to-large solutes such as, for example, myoglobin or circulating blood cytokines. Consequently, measurements of the effective delivered purification dose obtained using urea are not representative of the extracorporeal clearance of target solutes of dialysis treatments.

Yet another drawback lies in the fact that a delivered clearance calculation requires the use of complex mathematical models, which are often unknown to healthcare workers doing the sampling and requesting the analyses. This implies a higher risk of errors in the evaluation of the delivered clearance.

In light of the above observations as to the complexity of the sampling process, the long time necessary for sending the samples and executing laboratory analyses, and the complexity of the necessary mathematical calculations, the effective delivered purification dose is normally not, at present, quantified during clinical practice, despite the recommendations. Moreover, quantifying the extracorporeal clearance for urea alone limits the obtained information to solutes having a molecular size which is similar to that of such solute.

SUMMARY OF THE DISCLOSURE

It is therefore one object of the present invention to solve these and other problems of the prior art, and particularly to provide a method, an acquisition apparatus, an analysis apparatus and a system for acquiring liquid biological samples from an extracorporeal circuit for subjecting a patient to an extracorporeal blood purification treatment, which make it possible to automate the sampling process while reducing its complexity and increasing its safety.

It is another object of the present invention to provide a method, an acquisition apparatus, an analysis apparatus and a system for acquiring liquid biological samples from an extracorporeal circuit for subjecting a patient to an extracorporeal blood purification treatment, which make it possible to obtain results necessary for calculating the extracorporeal clearance in real time, or anyway in less time than with the prior art.

It is a further object of the present invention to provide a method, an acquisition apparatus, an analysis apparatus and a system for acquiring liquid biological samples from an extracorporeal circuit for subjecting a patient to an extracorporeal blood purification treatment, which permit quantifying the extracorporeal clearance for two or more solutes having a molecular size greater than or equal to that of urea.

In brief, the present invention relates to an automated acquisition of liquid biological samples from an extracorporeal circuit for subjecting a patient to an extracorporeal blood purification treatment, with automatic real-time determination of extracorporeal clearance values for solutes with small, medium and large molecular mass.

The advantageous features of the present invention are set out in the appended claims, which are an integral part of the present description.

BRIEF DESCRIPTION OF THE DRAWINGS

The invention will now be described in detail through some non-limiting exemplary embodiments thereof, with particular reference to the annexed drawings, wherein.

DETAILED DESCRIPTION OF THE PREFERRED EMBODIMENTS

Figure 1:
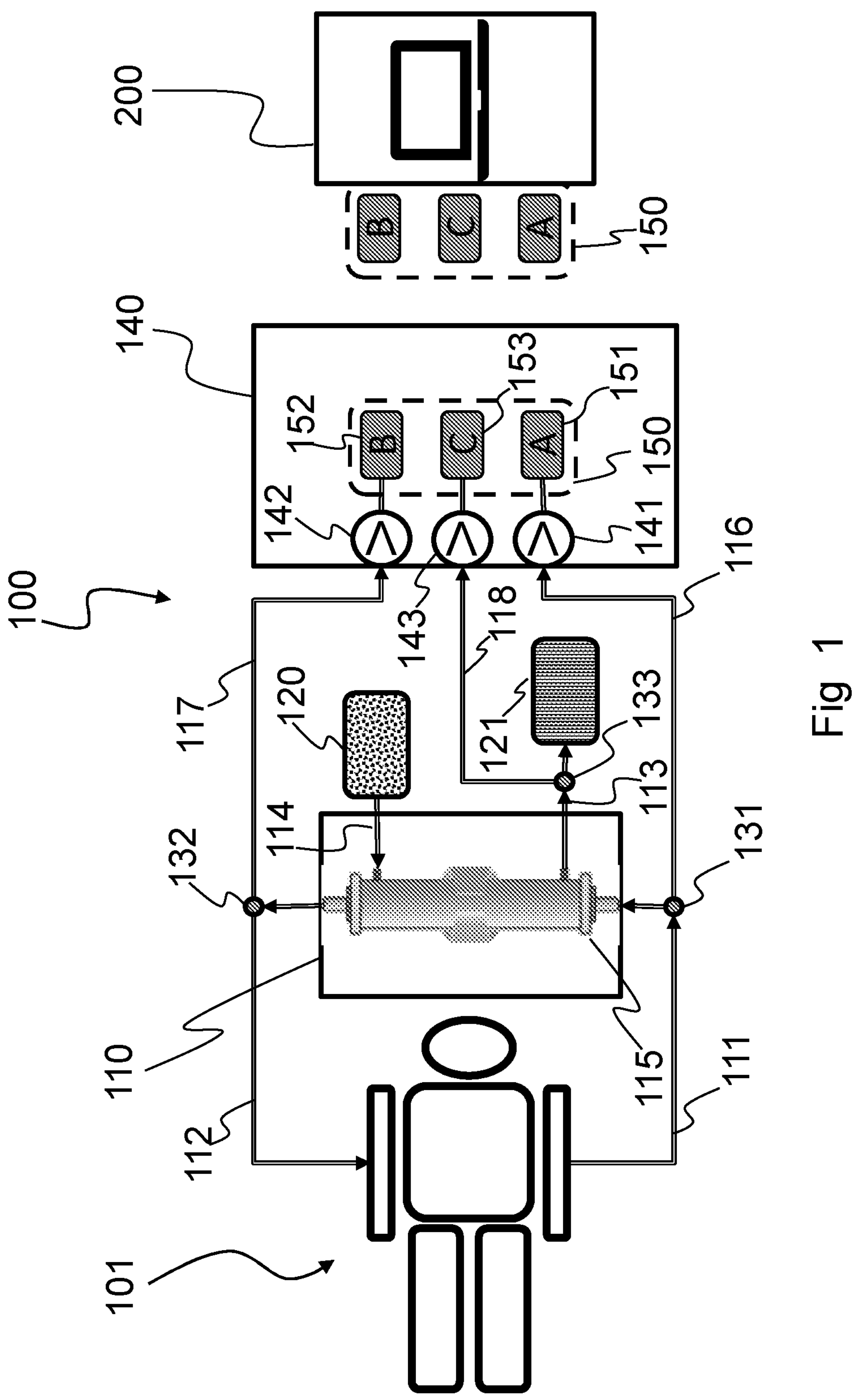
FIG. 1 schematically shows a system for acquiring liquid biological samples from an extracorporeal circuit for subjecting a patient to an extracorporeal blood purification treatment, according to one embodiment of the present invention.

With reference to FIG. 1, there is shown a system 100 for acquiring liquid biological samples from an extracorporeal circuit for subjecting a patient 101 to an extracorporeal blood purification treatment. The system 100 comprises a haemodialysis machine 110, an apparatus for acquisition of liquid biological samples 140, and an extracorporeal circuit, operatively connected to one another.

In addition, the system 100 may comprise an analysis apparatus 200 for analysing the biological samples acquired by the acquisition apparatus 140.

The haemodialysis machine 110, e.g. a CRRT (Continuous Renal Replacement Therapy) apparatus, comprises a haemodiafilter 115, which consists of a first compartment and a second compartment separated from each other by an artificial semi-permeable haemodiafiltration membrane. The blood tissue of the patient 101 under treatment flows in the first compartment, whereas either a saline solution with appropriate composition and concentration, called dialysis liquid (or dialysate), or waste liquid (effluent) flows in the second compartment. In the haemodiafilter 115, adjustment of the blood concentration of the solutes occurs by transmembrane passage of the latter between the blood tissue and the dialysate, in accordance with the physical principle of the concentration gradient, which tends to balance the concentration between blood tissue and dialysate. Moreover, through suitable adjustment of a transmembrane pressure gradient in the haemodiafilter 115, it is also possible to force the transmembrane passage of liquids and solutes dissolved therein. The haemodiafiltration membrane may be, for example, of cellulose or synthetic derivation.

The haemodialysis machine 110 comprises a first pump (not shown in FIG. 1), which provides circulation of the blood tissue from the patient 101 to the haemodiafilter 115 via a first hacmatic line 111 inputted to the haemodiafilter 115; the first pump also provides circulation of the blood tissue from the haemodiafilter 115 to the patient 101 via a second haematic line 112 outputted from the haemodiafilter 115. For example, the first haematic line 111 and the second haematic line 112 may comprise flexible and/or rigid tubes made of silicone, rubber or PVC, while the first pump may comprise a peristaltic pump.

In addition, the haemodialysis machine 110 comprises a second pump (not shown in FIG. 1), which provides circulation of the dialysate from a first tank 120, comprising clean dialysate, to the haemodiafilter 115 via an inlet line 114 inputted to the haemodiafilter 115; the second pump also provides circulation of the dialysate from the haemodiafilter 115 to a second tank 121, comprising exhausted dialysate, via an effluent line 113 outputted from the haemodiafilter 115. For example, the inlet line 114 and the effluent line 113 may comprise flexible and/or rigid tubes made of silicone, rubber or PVC, while the second pump may comprise a peristaltic pump.

The extracorporeal circuit comprises the haemodiafilter 115, the first haematic line 111 (inflow hacmatic line), the second hacmatic line 112 (outflow hacmatic line), the inlet line 114, the effluent line 113, vascular accesses, e.g. needles or catheters, and tubes and accessories for the circulation of blood tissue and dialysate in the haemodiafilter 115. In particular, the extracorporeal circuit comprises a first circuit comprising the first compartment of the haemodiafilter 115, the first haematic line 111 and the second hacmatic line 112; in addition, the extracorporeal circuit comprises a second circuit comprising the second compartment of the haemodiafilter 115, the inlet line 114 and the effluent line 113.

The first circuit and the second circuit are separated from each other by the semi-permeable hacmodiafiltration membrane.

In accordance with the present invention, the apparatus for acquisition of liquid biological samples 140 may comprise a first hydraulic machine 141, a second hydraulic machine 142 and a third hydraulic machine 143, which may each comprise, for example, an electrically operable peristaltic pump; the apparatus 140 further comprises a first collection chamber 151, a second collection chamber 152 and a third collection chamber 153.

The first collection chamber 151 is adapted to be in fluidic communication with a first sampling port 131 of the extracorporeal circuit via the first hydraulic machine 141, which may, for example, be operatively connected to the first sampling port 131 via a first connection line 116; the first sampling port 131 is operatively connected to the first haematic line 111 inputted to the haemodiafilter 115.

The second collection chamber 152 is adapted to be in fluidic communication with a second sampling port 132 of the extracorporeal circuit via the second hydraulic machine 142, which may, for example, be operatively connected to the second sampling port 132 via a second connection line 117; the second sampling port 132 is operatively connected to the second haematic line 112 outputted from the haemodiafilter 115.

The third collection chamber 153 is adapted to be in fluidic communication with a third sampling port 133 of the extracorporeal circuit via the third hydraulic machine 143, which may, for example, be operatively connected to the third sampling port 133 via a third connection line 118; the third sampling port 133 is operatively connected to the effluent line 113 of the haemodiafilter 115. The first connection line 116, the second connection line 117 and the third connection line 118 may comprise, for example, flexible and/or rigid tubes made of silicone, rubber or PVC.

For example, the first collection chamber 151, as well as the second collection chamber 152 and the third collection chamber 153, may be made of plastic or vitreous material, and may have a volume V ranging from 0.1 ml to 2 ml.

In particular, the first collection chamber 151, as well as the second collection chamber 152 and the third collection chamber 153, may comprise at least one aperture through which a material in the liquid state, such as blood tissue of the patient 101 or dialysate, can enter and/or exit; said aperture may comprise a lid adapted to hermetically seal the first collection chamber 151. In one embodiment of the invention, a needle and/or a cannula may be hermetically inserted into the lid, in fluidic communication with the first sampling port 131. For example, said lid may be made of elastic material, e.g. rubber and/or silicone, suitable for hermetically sealing the first collection chamber 151. The same examples of embodiment described above with reference to the first collection chamber 151 also apply, mutatis mutandis, to the second collection chamber 152 and the third collection chamber 153. In one embodiment of the invention, each one of the first collection chamber 151, second collection chamber 152 and third collection chamber 153 can be individually removed from the apparatus 140, independently of the other collection chambers 151, 152, 153. In addition, the first collection chamber 151, the second collection chamber 152 and the third collection chamber 153 may be either disposable or, as an alternative, reusable, e.g. after a sterilization process.

Additionally or alternatively, a storage unit 150 may comprise the first collection chamber 151, the second collection chamber 152 and the third collection chamber 153, wherein said storage unit 150 may be removable from the apparatus for acquisition of liquid biological samples 140. For example, the first collection chamber 151, the second collection chamber 152 and the third collection chamber 153 may be housed on a plastic support of the storage unit 150, suitably shaped to allow access to the needle and/or cannula into the lid of each one of the first collection chamber 151, second collection chamber 152 and third collection chamber 153.

In this manner, in accordance with the present invention, the first hydraulic machine 141 is adapted to fill the first collection chamber 151 with a first biological sample A, the second hydraulic machine 142 is adapted to fill the second collection chamber 152 with a second biological sample B, and the third hydraulic machine 143 is adapted to fill the third collection chamber 153 with a third biological sample C. In particular, the first biological sample A may comprise a sample of blood tissue coming from the first hacmatic line 111 inputted to the haemodiafilter 115, the second biological sample B may comprise a sample of blood tissue coming from the second haematic line 112 outputted from the haemodiafilter 115, and the third biological sample C may comprise a sample of exhausted dialysate coming from the effluent line 113 outputted from haemodiafilter 115.

Advantageously, in accordance with the present invention, the first hydraulic machine 141, the second hydraulic machine 142 and the third hydraulic machine 143 can be activated at the same time with a flow rate value P.

For example, the first hydraulic machine 141, the second hydraulic machine 142 and the third hydraulic machine 143 can be electrically controlled by a control unit of the apparatus 140, c.g. comprising a control unit that activates them simultaneously for a sampling time interval T. For example, the first hydraulic machine 141, the second hydraulic machine 142 and the third hydraulic machine 143 may be activated simultaneously upon receiving an electric command signal generated by a healthcare professional by means of a sampling start button included in the apparatus 140. Said flow rate value P may, for example, for each one of the first hydraulic machine 141, second hydraulic machine 142 and third hydraulic machine 143, range from 0.1 ml/min to 2 ml/min, and can be set via control means of said first hydraulic machine 141, second hydraulic machine 142 and third hydraulic machine 143. Consequently, the sampling time interval T can be determined on the basis of the flow rate value P and the volume V of each one of the first collection chamber 151, second collection chamber 152 and third collection chamber 153, e.g. according to the following relation: T=V/P, expressed in minutes.

The apparatus for acquisition of liquid biological samples 140 according to the present invention advantageously permits sampling the first biological sample A, the second biological sample B and the third biological sample C with much higher precision than can be obtained with the currently known manual method involving three healthcare professionals. In addition, the apparatus for acquisition of liquid biological samples 140 according to the present invention advantageously ensures a considerable reduction in the biological risks incurred by the healthcare personnel performing said manual method.

Figure 2:
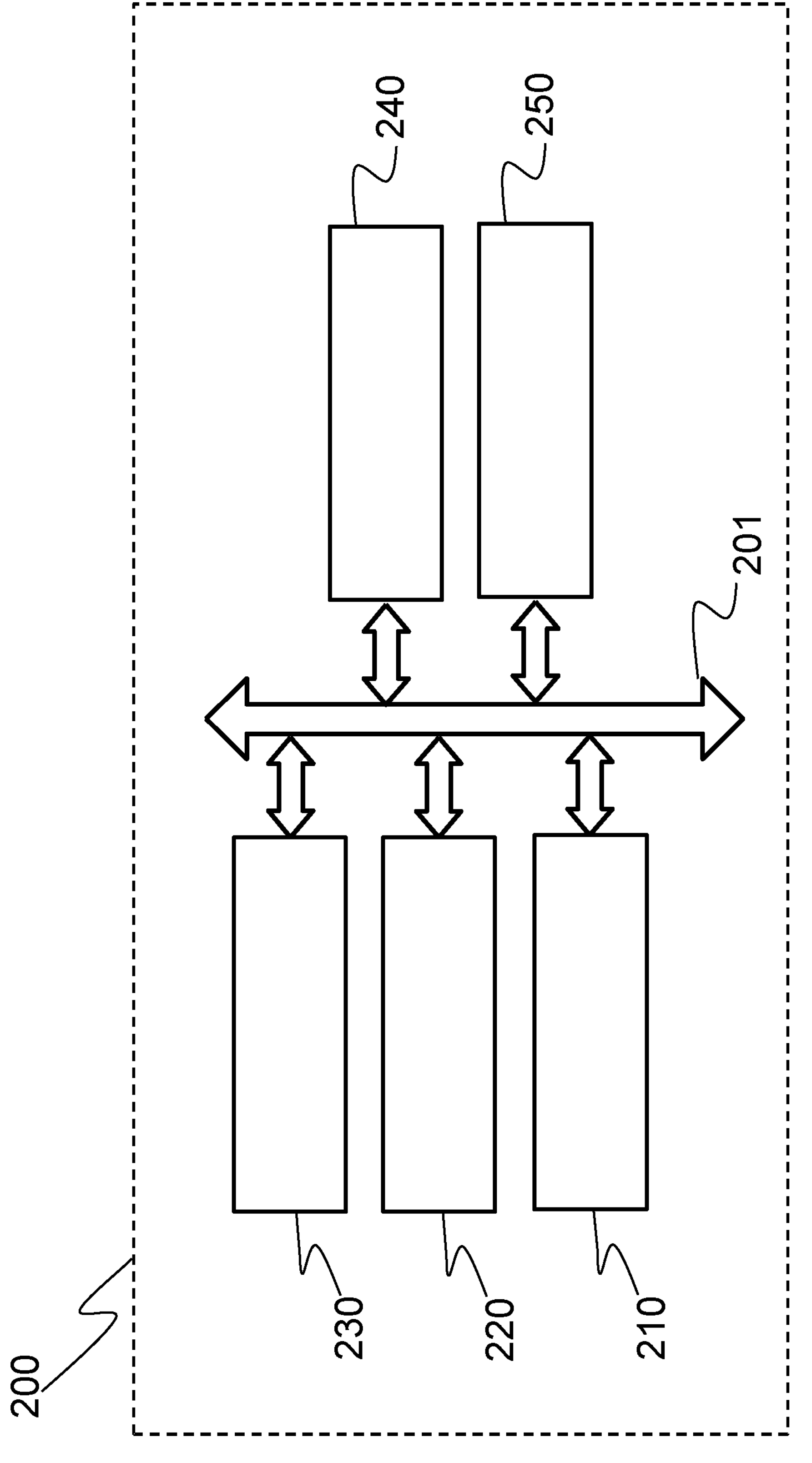
FIG. 2 shows an illustrative block diagram of an analysis apparatus of the system of FIG. 1.

FIG. 2 shows an illustrative block diagram of an analysis apparatus 200 for analysing the first biological sample A, the second biological sample B and the third biological sample C, in accordance with the present embodiment of the invention. Said analysis apparatus 200 may comprise actuator means 210, sensor means 220, interface means 230, memory means 240, and processing means 250. These can be interconnected by means of a communication bus 201.

The actuator means 210 are adapted to perform physical and/or chemical operations on at least one of said first biological sample A, second biological sample B and third biological sample C within the analysis apparatus 200.

For example, the actuator means 210 can execute at least one of the following physical and/or chemical operations: handling, centrifugation, partitioning, heating and cooling, mixing with one or more chemical substances. In addition, the actuator means 210 may execute analysis methods on at least one of said first biological sample A, second biological sample B and third biological sample C within the analysis apparatus 200. In particular, the actuator means 210 may execute one or more of the following analysis methods: immunofluorimetric method, colorimetric method, UV method, electrochemical method, immunoturbidimetric method, and potentiometric method. The actuator means 210 may comprise one or more of the following devices: electromechanical servo mechanisms, electric servo motors, self-moving prehensile arms, electric pumps, UV lamps, IR lamps, LASER sources, cooling apparatuses, and heating apparatuses.

The sensor means 220 are adapted to measure one or more physical quantities concerning at least one of said first biological sample A, second biological sample B, third biological sample C, and any further samples that may be derived therefrom. The sensor means 220 may comprise one or more of the following sensors: an inertial measurement unit (IMU), a gyroscope, an accelerometer, an altimeter, a thermometer, a barometer, a piezoelectric sensor, an extensometer, a load cell, a voltmeter, an ammeter, a spectrometer, a pH meter.

The interface means 230 are adapted to operatively connect an operator for managing and configuring the analysis apparatus 200. The interface means 230 may comprise, for example, a keyboard, a screen, a touchscreen, a mouse device, and so forth.

In addition, the interface means 230 may also comprise communication means allowing communication between the analysis apparatus 200 and a server (not shown in FIG. 2). The communication means may comprise, for example, an Ethernet interface, a WiFi interface, a USB interface, a mobile network interface (GSM, UMTS, LTE, 5G), and so forth.

The memory means 240 are adapted to store information and instructions of the analysis apparatus 200.

Such information may comprise data and/or parameters relating to the actuator means 210, the sensor means 220 and the interface means 230. The instructions stored in the memory means 240 will be described in detail later on with reference to the flow chart of FIG. 3. The memory means 240 may comprise, for example, a Flash-type solid-state memory.

The processing means 250 are adapted to process the information and the instructions stored in the memory means 240, relating to the interface means 230, the sensor means 220 and the actuator means 210, and may comprise, for example, a multicore ARM processor, a microcontroller, etc. The communication bus 201 is adapted to interconnect said memory means 240, interface means 230, sensor means 220 and actuator means 210 with the processing means 250.

In accordance with the present invention, the actuator means 210, the interface means 230, the sensor means 220, the memory means 240 and the processing means 250 are adapted to execute all the operations that are necessary to analyse the first biological sample A, the second biological sample B and the third biological sample C.

In particular, the actuator means 210 are adapted to receive the first collection chamber 151 comprising the first biological sample A, the second collection chamber 152 comprising the second biological sample B, and the third collection chamber 153 comprising the third biological sample C. For example, said first collection chamber 151, second collection chamber 152 and third collection chamber 153 may be housed, one at a time, in an inlet section of the analysis apparatus 200 comprising, for example, an inlet box or an inlet slot. Alternatively, said first collection chamber 151, second collection chamber 152 and third collection chamber 153 may be housed together at the same time in the inlet section of the analysis apparatus 200, e.g. by means of the storage unit 150 comprising the first collection chamber 151, the second collection chamber 152 and the third collection chamber 153. In particular, the storage unit 150 can be introduced into the analysis apparatus 200 and then removed from said analysis apparatus 200 upon completion of the analysis of the first biological sample A, second biological sample B and third biological sample C.

In addition, the actuator means 210 are adapted to subdivide each one of said first biological sample A, second biological sample B and third biological sample C into at least a first share A1, B1,C1, a second share A2, B2, C2 and a third share A3, B3, C3. For example, each biological sample A, B and C may be taken in equal volumes from each one of said first collection chamber 151, second collection chamber 152 and third collection chamber 153 and poured into at least two or more test tubes, e.g. made of glass, of the analysis apparatus 200, so that each first share A1, B1, C1, second share A2, B2, C2 and third share A3, B3, C3 can be analysed, by the sensor means 220, in accordance with one or more of the following methods: immunofluorimetric method, colorimetric method, UV method, electrochemical method, immunoturbidimetric method, and potentiometric method. In particular, the first share A1, B1, C1 may concern a first solute having a first molecular mass value of 0 to 500 dalton, while the second share A2, B2, C2 may concern a second solute having a second molecular mass value of 501 to 5,000 dalton, and, finally, the third share A3, B3, C3 may concern a third solute having a third molecular mass value of 5,001 to 100,000 dalton. The following table shows an example of possible first, second and third solutes that can be analysed by the analysis apparatus 200 according to the present invention.

TABLE 1

| | Solute name | Molecular mass | Method of analysis |
|---|---|---|---|
| First solute (small) | Urea | 60 Da | Colorimetric Kinetic |
| | Fluoride ion | 42 Da | Ion Selective Probe |
| | Creatinine | 113 Da | Colorimetric Kinetic |
| Second solute (medium) | Cystatin C | 13 kDa | Immunophelometric |
| | Myoglobin | 16.7 kDa | Chemiluminescent Immunoassay |
| | B2 Microglobulin | 11 kDa | Chemiluminescent Immunoassay |
| | Vitamin B12 | 1.3 kDa | Chemiluminescent Immunoassay |
| Third solute (large) | Albumin | 66.5 kDa | Colorimetric |
| | Interleukin 18 (IL-18) | 24 kDa | ELISA |
| | Kidney Injury Molecule-1 (KIM-1) | 65-110 kDa | ELISA |

For example, the methods of analysis listed in Table 1 can be executed simultaneously on said first share A1, B1, C1, second share A2, B2, C2 and third share A3, B3, C3.

In addition, following the above-listed analyses, the sensor means 220 are adapted to determine, for each first share A1, B1, C1, second share A2, B2, C2 and third share A3, B3, C3,concentration values of the first solute C_A1, C_B1, C_C1, concentration values of the second solute C_A2, C_B2, C_C2, and concentration values of the third solute C_A3, C_B3, C_C3, e.g. expressed in mg/l. For example, such concentration values C_A1, C_B1, C_C1, C_A2, C_B2, C_C2, C_A3,C_B3 and C_C3 can be determined, via the sensor means 220, in accordance with one or more of the following methods: immunofluorimetric method, colorimetric method, UV method, electrochemical method, immunoturbidimetric method, and potentiometric method.

The processing means 250 are adapted to determine a first mass balance error Err1, a second mass balance error Err2 and a third mass balance error Err3 on the basis of at least one of said concentration values of the first solute C_A1, C_B1, C_C1, concentration values of the second solute C_A2, C_B2, C_C2 and concentration values of the third solute C_A3, C_B3, C_C3. In particular, the first mass balance error Err1 concerns the first solute, the second mass balance error Err2 concerns the second solute, and the third mass balance error Err3 concerns the third solute. For example, the first mass balance error Err1, the second mass balance error Err2 and the third mass balance error Err3 can be expressed as percentage and determined in accordance with the following relations:

$$Err1 = (M\_A1 - M\_B1 - M\_C1)/M\_A1; \quad 1)$$

$$Err2 = (M\_A2 - M\_B2 - M\_C2)/M\_A2;$$

$$Err3 = (M\_A3 - M\_B3 - M\_C3)/M\_A3,$$

where M_A1, M_B1, M_C1, M_A2, M_B2, M_C2, M_A3, M_B3 and M_C3 indicate mass values of the first solute, second solute and third solute for, respectively, the shares A1,B1, C1, A2, B2, C2, A3, B3 and C3. For example, such mass values M_A1, M_B1, M_C1,M_A2, M_B2, M_C2, M_A3, M_B3 and M_C3 can be determined by means of the following relations:

$$M\_A1 = C\_A1 * Q\_A1 * t; \quad 2)$$

$$M\_B1 = C\_B1 * Q\_B1 * t;$$

$$M\_C1 = C\_C1 * Q\_C1 * t;$$

-continued $$M\_A2 = C\_A2 * Q\_A2 * t;$$

$$M\_B2 = C\_B2 * Q\_B2 * t;$$

$$M\_C2 = C\_C2 * Q\_C2 * t;$$

$$M\_A3 = C\_A3 * Q\_A3 * t;$$

$$M\_B3 = C\_B3 * Q\_B3 * t;$$

$$M\_C3 = C\_C3 * Q\_C3 * t,$$

where Q_A1, Q_B1, Q_C1, Q_A2, Q_B2, Q_C2, Q_A3, Q_B3 and Q_C3 indicate flow values for, respectively, the shares A1, B1, C1, A2, B2, C2, A3, B3 and C3, which can be obtained from the haemodialysis machine 110 during the haemodialysis process in a given time interval t, e.g. expressed in ml/h.

In addition, the processing means 250 are adapted to determine, for each one of said first solute, second solute and third solute, a clearance value K1, K2, K3 and/or a sieving coefficient H1,H2, H3 when each one of said first mass balance error Err1, second mass balance error Err2 and third mass balance error Err3 is comprised between −10% and +10%.

For example, such clearance values K1, K2 and K3 can be determined in accordance with the following relations:

$$K1 = \left(Qb\frac{C\_A1 - C\_B1}{C\_A1} + Quf\frac{2\ C\_B1}{C\_A1 + C\_B1}\right); \quad 3)$$

$$K2 = \left(Qb\frac{C\_A2 - C\_B2}{C\_A2} + Quf\frac{2\ C\_B2}{C\_A2 + C\_B2}\right);$$

$$K3 = \left(Qb\frac{C\_A3 - C\_B3}{C\_A3} + Quf\frac{2\ C\_B3}{C\_A3 + C\_B3}\right),$$

where C_A1, C_B1, C_A2, C_B2, C_A3 and C_B3 are concentration values of the first solute, second solute and third solute for, respectively, the shares A1, B1, A2, B2, A3 and B3.

For example, such concentration values C_A1, C_B1, C_A2, C_B2, C_A3 and C_B3 can be determined, via the sensor means 220, in accordance with one or more of the following methods: immunofluorimetric method, colorimetric method, UV method, electrochemical method, immunoturbidimetric method, and potentiometric method.

In particular, Qb indicates a blood flow value expressed in ml/min, while Quf indicates an ultrafiltration flow value that can be determined as: Quf=Qr_pre+Qr_post+Qnet, where Qr_pre is a pre-dilution replacement flow value expressed in ml/h, Qr_post is a post-dilution replacement flow value expressed in ml/h, and Qnet is a net ultrafiltration flow value expressed in ml/h. Such values of Qr_pre, Qr_post, Qnet and Qb can be obtained from the haemodialysis machine 110 during the haemodialysis process.

Advantageously, in accordance with the present invention, the clearance values K1, K2, K3 make it possible to directly assess: I) an instantaneous clearance value of solutes having different molecular mass, i.e. small, medium, large (see Table 1); II) the variation of such clearance value over time; III) the variations of such clearance value measured on the solutes (current effective delivered dose) compared with the clearance estimated from the effluent flow (current dose), which can be calculated as: currentDose=Qr_pre+Qr_post+Qnet+Qd, where Qd is a dialysate flow value expressed in ml/h, obtainable from the haemodialysis machine 110 during the haemodialysis process. It is also possible to assess in a simple and immediate manner how the prescription variations of the flows Qr_pre, Qr_post, Qnet and Qb of the haemodialysis machine 110 affect the actual clearance of the different target solutes.

Additionally or alternatively, the processing means 250 are adapted to determine, for each one of said first solute, second solute and third solute, a sieving coefficient H1, H2, H3, which can be determined in accordance with the following relations:

$$H1 = \frac{2\ C\_C1}{C\_A1 + C\_B1}; \quad 4)$$

$$H2 = \frac{2\ C\_C2}{C\_A2 + C\_B2};$$

$$H3 = \frac{2\ C\_C3}{C\_A3 + C\_B3},$$

where C_C1, C_C2 and C_C3 are the concentration values of the first solute, second solute and third solute for, respectively, the shares C1, C2 and C3. For example, such concentration values C_C1, C_C2 and C_C3 can be determined, via the sensor means 220, in accordance with one or more of the following methods: immunofluorimetric method, colorimetric method, UV method, electrochemical method, immunoturbidimetric method, and potentiometric method. In the haemodialysis treatments context, such sieving coefficients H1, H2, H3 are known as effluent saturation coefficient, and can be determined in accordance with Relation 4).

Advantageously, according to the present invention, the sieving coefficients H1, H2, H3 make it possible to evaluate the fouling effect on the haemodiafiltration membrane, e.g. by means of a graphic comparison in which such sieving coefficients H1, H2, H3, obtainable from different measurements taken in different time intervals, are superimposed.

It will be apparent to a person skilled in the art that, in accordance with the present invention, one or more further solutes may be considered in addition to the first solute, second solute and third solute, for the purpose of determining one or more further clearance values and/or one or more sieving coefficients. This advantageously permits a more effective evaluation of the fouling effect on the haemodiafiltration membrane. Such one or more further solutes may have a molecular mass value in the range of 0 to 100,000 dalton.

In accordance with the present invention, the analysis apparatus 200 may be replaced with two or more apparatuses, known in the art, which together perform the operations that are necessary for analysing the first biological sample A, the second biological sample B and the third biological sample C as previously described herein with reference to the analysis apparatus 200. For example, a first apparatus may subdivide each one of said first biological sample A, second biological sample B and third biological sample C into the first share A1, B1, C1, second share A2, B2, C2 and third share A3, B3, C3. Subsequently, a second apparatus may separately analyse the first share A1, B1, C1, the second share A2, B2, C2 and the third share A3, B3, C3 to obtain the first mass balance error Err1,the second mass balance error Err2 and the third mass balance error Err3 in accordance with Relations 1). Finally, a third apparatus may determine, for each one of said first solute, second solute and third solute, the clearance value K1, K2, K3 and/or the sieving coefficient H1, H2, H3, e.g. in accordance with, respectively, Relations 3) and 4), when each one of said first mass balance error Err1, second mass balance error Err2 and third mass balance error Err3 is comprised between −10% and +10%.

Figure 3:
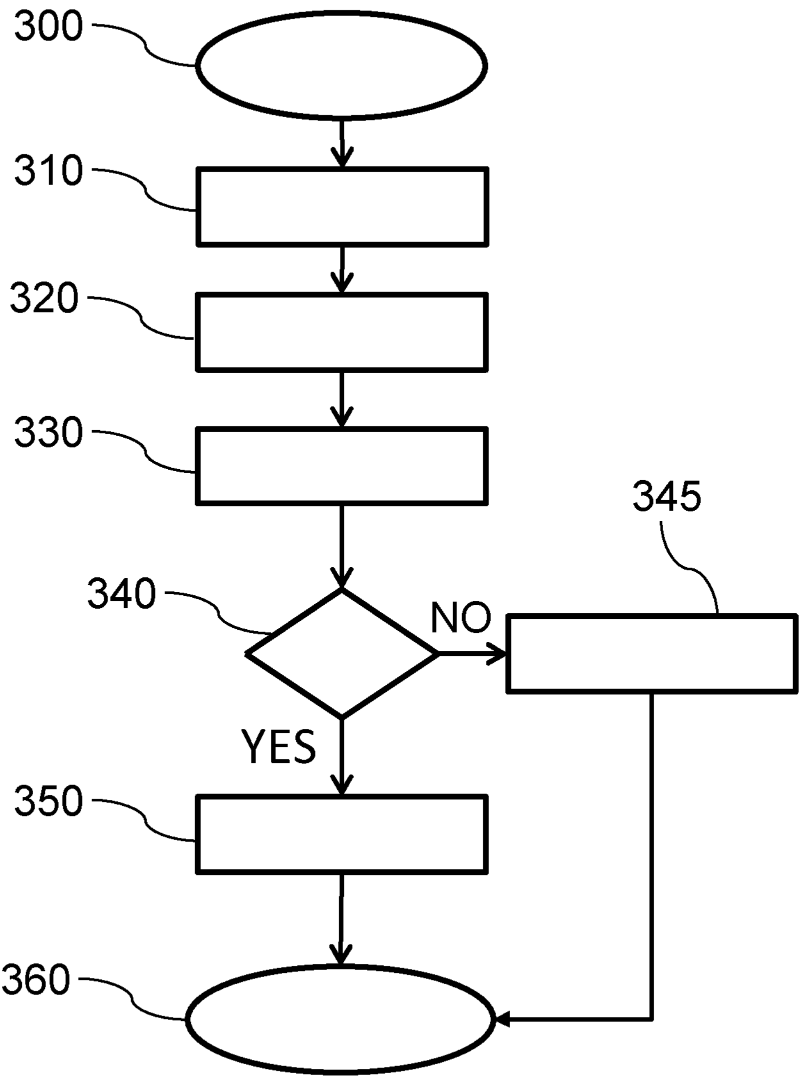
FIG. 3 shows an illustrative flow chart of a method of acquiring liquid biological samples from an extracorporeal circuit for subjecting a patient to an extracorporeal blood purification treatment, in accordance with the present embodiment of the invention.

With reference to FIG. 3, the following will describe a method of acquiring liquid biological samples from an extracorporeal circuit for subjecting the patient 101 to an extracorporeal blood purification treatment.

At step 300 an initialization phase is carried out, in which the haemodialysis machine 110 and the apparatus for acquisition of liquid biological samples 140 are operatively connected to the extracorporeal circuit, e.g. by a healthcare professional. During this phase, the healthcare professional may initialize both the haemodialysis machine 110, for subjecting the patient 101 to the haemodialysis treatment, and the apparatus for acquisition of liquid biological samples 140.

During this phase, the healthcare professional may also initialize the analysis apparatus 200, e.g. by subjecting the analysis apparatus 200 to a sterilization process.

At step 310 a sampling phase is carried out, in which the first sampling port 131 of the extracorporeal circuit is in fluidic communication with the first collection chamber 151 via the first hydraulic machine 141 of the acquisition apparatus 140; in particular, the first sampling port 131 is operatively connected to the first haematic line 111 inputted to the haemodiafilter 115 of the extracorporeal circuit. The second sampling port 132 of the extracorporeal circuit is in fluidic communication with the second collection chamber 152 via the second hydraulic machine 142 of the acquisition apparatus 140; in particular, the second sampling port 132 is operatively connected to the second haematic line 112 outputted from the haemodiafilter 115. The third sampling port 133 of the extracorporeal circuit is in fluidic communication with the third collection chamber 153 via the third hydraulic machine 143 of the acquisition apparatus 140; in particular, the third sampling port 133 is operatively connected to the effluent line 113 of the haemodiafilter 115.

During this phase, the first hydraulic machine 141 fills the first collection chamber 151 with the first biological sample A, while the second hydraulic machine 142 fills the second collection chamber 152 with the second biological sample B and the third hydraulic machine 143 fills the third collection chamber 153 with the third biological sample C. Advantageously, the first hydraulic machine 141, the second hydraulic machine 142 and the third hydraulic machine 143 are activated simultaneously and with the flow rate value P, which may preferably be, for example, in the range of 0.1 ml/min to 2 ml/min, and which can be set via control means of said first hydraulic machine 141, second hydraulic machine 142 and third hydraulic machine 143.

During this phase, for example, the first hydraulic machine 141, the second hydraulic machine 142 and the third hydraulic machine 143 can be electrically controlled by a control unit of the apparatus 140, e.g. comprising a control unit that activates them simultaneously for the sampling time interval T.

For example, the first hydraulic machine 141, the second hydraulic machine 142 and the third hydraulic machine 143 can be activated at the same time upon receiving an electric command signal generated by the healthcare professional by means of a sampling start button included in the apparatus 140. Consequently, the sampling time interval T may be determined, for example, on the basis of the flow rate value P and the volume V of each one of the first collection chamber 151, second collection chamber 152 and third collection chamber 153, e.g. in accordance with the following relation: T=V/P, expressed in minutes.

The apparatus for acquisition of liquid biological samples 140 according to the present invention advantageously permits sampling the first biological sample A, the second biological sample B and the third biological sample C with much higher precision than can be obtained with the currently known manual method involving three healthcare professionals. In addition, the apparatus for acquisition of liquid biological samples 140 according to the present invention advantageously ensures a considerable reduction in the biological risks incurred by the healthcare personnel performing said manual method.

In accordance with the present invention, the following steps may additionally be carried out.

At step 320 a phase of analysing the first biological sample A, the second biological sample B and the third biological sample C is carried out. For example, the first biological sample A, the second biological sample B and the third biological sample C, when housed in the storage unit 150, can be extracted simultaneously from the acquisition apparatus 140 and then transferred into the analysis apparatus 200. As an alternative, the first biological sample A, the second biological sample B and the third biological sample C may be transferred individually into the analysis apparatus 200, one at a time. During this phase, each one of said first biological sample A, second biological sample B and third biological sample C is subdivided into at least the first share A1, B1, C1, the second share A2, B2, C2 and the third share A3, B3, C3, wherein the first share Al, B1, CI concerns the first solute having the first molecular mass value of 0 to 500 dalton, the second share A2, B2, C2 concerns the second solute having the second molecular mass value of 501 to 5,000 dalton, and the third share A3,B3, C3 concerns the third solute having the third molecular mass value of 5,001 to 100,000 dalton. For example, cach biological sample A, B and C may be taken in equal volumes from each one of said first collection chamber 151, second collection chamber 152 and third collection chamber 153 and then poured into two or more test tubes, e.g. made of glass, of the analysis apparatus 200, so that cach first share A1, B1, C1, second share A2, B2, C2 and third share A3, B3, C3 can be analysed, via the sensor means 220, in accordance with one or more of the following methods: immunofluorimetric method, colorimetric method, UV method, electrochemical method, immunoturbidimetric method, and potentiometric method. During this step, e.g. using the above-mentioned methods of analysis, for cach first share Al, B1, C1, second share A2, B2, C2 and third share A3, B3, C3 the concentration values of the first solute C_A1, C_B1, C_C1, the concentration values of the second solute C_A2,C_B2, C_C2, and the concentration values of the third solute C_A3, C_B3, C_C3 are determined. For example, each one of said concentration values of the first solute C_A1, C_B1, C_C1, concentration values of the second solute C_A2, C_B2, C_C2 and concentration values of the third solute C_A3,C_B3, C_C3 are determined, via the sensor means 220, in accordance with one or more of the following methods: immunofluorimetric method, colorimetric method, UV method, electrochemical method, immunoturbidimetric method, potentiometric method.

At step 330 a first processing phase is carried out, in which the first mass balance error Err1, the second mass balance error Err2 and the third mass balance error Err3 are determined on the basis of at least one of said concentration values of the first solute C_A1, C_B1, C_C1, concentration values of the second solute C_A2, C_B2, C_C2 and concentration values of the third solute C_A3,C_B3, C_C3; wherein the first mass balance error Err1 concerns the first solute, the second mass balance error Err2 concerns the second solute, and the third mass balance error Err3 concerns the third solute. For example, the first mass balance error Err1, the second mass balance error Err2 and the third mass balance error Err3 may be expressed as percentage and determined in accordance with Relations 1) and 2).

At step 340, the processing means 250 verify whether each one of said first mass balance error Err1, second mass balance error Err2 and third mass balance error Err3 is comprised between- 10% and +10%. If so, they will execute step 350, otherwise they will execute step 345.

At step 345, the interface means 230 issue an error message to warn the operator that the first mass balance error Err1, the second mass balance error Err2 and the third mass balance error Err3exceed cach 5% in absolute value. For example, said error message may be displayed on a screen of the interface means 230. Subsequently, step 360 will be carried out.

At step 350 a second processing phase is carried out, in which, for each one of said first solute, second solute and third solute, a clearance value K1, K2, K3 and/or a sieving coefficient H1,H2, H3 are determined, e.g. in accordance with Relations 2) and 3), respectively.

At step 360, the processing means 250 execute a termination phase, in which all the operations that are necessary for terminating the method according to the present invention are carried out. For example, during this phase the first mass balance error Err1, the second mass balance error Err2 and the third mass balance error Err3 may be stored into the memory means 240 and/or displayed by the healthcare personnel on the screen of the interface means 230. In addition, the clearance values K1, K2, K3 and/or the sieving coefficients H1, H2, H3 may be stored into the memory means 240 and/or displayed by the healthcare professional on the screen of the interface means 230. For example, at the end of this phase the analysis apparatus 200 may carry out all the operations that are necessary for cleaning and/or sterilizing the actuator means 210 and the sensor means 220.

One or more phases of the method described above with reference to FIG. 3 can be implemented, for example, by means of a computer program product comprising portions of software code, which can be loaded into a memory of a terminal, such as, for example, a computer, a tablet, a Raspberry PI unit, etc., such terminal being usable for controlling the acquisition apparatus 140 and/or the analysis apparatus 200.

Advantageously, in accordance with the present invention, the clearance values K1, K2,K3 permit a direct evaluation of: I) an instantaneous clearance value of solutes having different molecular mass, i.e. small, medium and large (see Table 1); II) the variation of such clearance value over time; III) the variations of such clearance value measured on the solutes (current effective delivered dose) compared with the clearance estimated from the effluent flow (current dose). Moreover, in accordance with the present invention, the sieving coefficients H1, H2, H3advantageously make it possible to evaluate the fouling effect on the haemodiafiltration membrane, e.g. by means of a graphic comparison in which such sieving coefficients H1, H2, H3, obtainable from different measurements taken in different time intervals, are superimposed.

The advantages of the present invention are apparent from the above description.

The present invention provides a method, an acquisition apparatus, an analysis apparatus and a system for acquiring liquid biological samples from an extracorporeal circuit for subjecting a patient to an extracorporeal blood purification treatment which, advantageously, make it possible to automate the process of sampling biological samples by means of the first hydraulic machine, the second hydraulic machine and the third hydraulic machine, which can be activated at the same time with a flow rate value.

Another advantage of the present invention lies in the fact that it provides a method, an acquisition apparatus, an analysis apparatus and a system for acquiring liquid biological samples from an extracorporeal circuit for subjecting a patient to an extracorporeal blood purification treatment which, advantageously, permit quantifying the extracorporeal clearance for two or more solutes having a molecular size greater than or equal to that of urea. In fact, the clearance values obtained in accordance with the present invention advantageously permit a direct evaluation of the instantaneous clearance of solutes having different molecular mass (small, medium and large), the variation of the clearance value over time, and the variations of the clearance values measured on the solutes (current effective delivered dose) compared with the clearance estimated from the effluent flow (current dose).

A further advantage of the present invention comes from the fact that it provides a method, an acquisition apparatus, an analysis apparatus and a system for acquiring liquid biological samples from an extracorporeal circuit for subjecting a patient to an extracorporeal blood purification treatment which, advantageously, permit obtaining the extracorporeal clearance in real time, or anyway in less time than with the prior art, since the acquired biological samples can be easily handled by the operator and easily analysed in accordance with the above description of the present invention.

Of course, without prejudice to the principle of the present invention, the forms of embodiment and the implementation details may be extensively varied from those described and illustrated herein merely by way of non-limiting example, without however departing from the protection scope of the present invention as set out in the appended claims.

The invention claimed is:

1. A method of acquiring liquid biological samples from an extracorporeal circuit for subjecting a patient to an extracorporeal blood purification treatment, said method comprising a sampling phase wherein:

I) a first sampling port of said extracorporeal circuit is in fluidic communication with a first collection chamber via a first hydraulic machine, said first sampling port being operatively connected to a first haematic line inputted to a haemodiafilter of said extracorporeal circuit;

II) a second sampling port of said extracorporeal circuit is in fluidic communication with a second collection chamber via a second hydraulic machine, said second sampling port being operatively connected to a second haematic line outputted from said haemodiafilter;

III) a third sampling port of said extracorporeal circuit is in fluidic communication with a third collection chamber via a third hydraulic machine, said third sampling port being operatively connected to an effluent line of said haemodiafilter, wherein said first hydraulic machine fills said first collection chamber with a first biological sample (A), said second hydraulic machine fills said second collection chamber with a second biological sample (B), and said third hydraulic machine fills said third collection chamber with a third biological sample (C), said first hydraulic machine, said second hydraulic machine and said third hydraulic machine being activated at the same time and with a flow rate value (P).

2. The method according to claim 1, comprising:

an analysis phase, in which each one of said first biological sample (A), second biological sample (B) and third biological sample (C) are respectively subdivided into at least a first share (A1, B1, C1), a second share (A2, B2, C2) and a third share (A3, B3, C3), wherein said first share (A1, B1, C1) concerns a first solute having a first molecular mass value of 0to 500 dalton, said second share (A2, B2, C2) concerns a second solute having a second molecular mass value of 501 to 5,000 dalton, and said third share (A3, B3, C3) concerns a third solute having a third molecular mass value of 5,001 to 100,000 dalton, and wherein concentration values of the first solute (C_A1, C_B1, C_C1), concentration values of the second solute (C_A2, C_B2, C_C2) and concentration values of the third solute (C_A3, C_B3, C_C3) are determined for each first share (A1, B1, C1), second share (A2, B2, C2) and third share (A3, B3, C3);

a first processing phase, in which a first mass balance error (Err1), a second mass balance error (Err2) and a third mass balance error (Err3) are determined on the basis of at least one of said concentration values of the first solute (C_A1, C_B1, C_C1), concentration values of the second solute (C_A2, C_B2, C_C2) and concentration values of the third solute (C_A3, C_B3, C_C3), said first mass balance error (Err1) concerning said first solute, said second mass balance error (Err2) concerning said second solute, and said third mass balance error (Err3) concerning said third solute;

a second processing phase, in which, for each one of said first solute, second solute and third solute, a clearance value (K1, K2, K3) and/or a sieving coefficient (H1, H2, H3) or an effluent saturation coefficient are determined when each one of said first mass balance error (Err1), second mass balance error (Err2) and third mass balance error (Err3) is comprised between −10% and +10%.

3. The method according to claim 2, wherein each one of said concentration values of the first solute (C_A1, C_B1, C_C1), concentration values of the second solute (C_A2, C_B2, C_C2) and concentration values of the third solute (C_A3, C_B3, C_C3) are determined in accordance with one or more of the following methods:

immunofluorimetric method, colorimetric method, UV method, electrochemical method, immunoturbidimetric method, potentiometric method.

4. An apparatus for acquisition of liquid biological samples from an extracorporeal circuit for subjecting a patient to an extracorporeal blood purification treatment, said apparatus comprising a first hydraulic machine, a second hydraulic machine, a third hydraulic machine, and comprising:

I) a first collection chamber adapted to be in fluidic communication with a first sampling port of said extracorporeal circuit via said first hydraulic machine, said first sampling port being operatively connected to a first haematic line inputted to a haemodiafilter of said extracorporeal circuit;

II) a second collection chamber adapted to be in fluidic communication with a second sampling port of said extracorporeal circuit via said second hydraulic machine, said second sampling port being operatively connected to a second haematic line outputted from said haemodiafilter;

III) a third collection chamber adapted to be in fluidic communication with a third sampling port of said extracorporeal circuit via said third hydraulic machine, said third sampling port being operatively connected to an effluent line of said haemodiafilter, said apparatus being characterized in that said first hydraulic machine is adapted to fill said first collection chamber with a first biological sample (A), said second hydraulic machine is adapted to fill said second collection chamber with a second biological sample (B), and said third hydraulic machine is adapted to fill said third collection chamber with a third biological sample (C), said first hydraulic machine, said second hydraulic machine and said third hydraulic machine being activable at the same time and with a flow rate value.

5. The acquisition apparatus according to claim 4, wherein a storage unit comprises said first collection chamber, said second collection chamber and said third collection chamber, said storage unit being removable from said apparatus for acquisition of liquid biological samples.

6. An analysis apparatus comprising actuator means, sensor means, memory means, and processing means adapted to:

receive a first collection chamber comprising a first biological sample (A), a second collection chamber comprising a second biological sample (B), and a third collection chamber comprising a third biological sample (C);

subdivide each one of said first biological sample (A), second biological sample (B) and third biological sample (C), respectively, into at least a first share (A1, B1, C1), a second share (A2, B2, C2) and a third share (A3, B3, C3), said first share (A1, B1, C1) concerning a first solute having a first molecular mass value of 0 to 500 dalton, said second share (A2, B2, C2) concerning a second solute having a second molecular mass value of 501 to 5,000 dalton, and said third share (A3, B3, C3) concerning a third solute having a third molecular mass value of 5,001 to 100,000 dalton;

determine, for each one of said first share (A1, B1, C1), second share (A2, B2, C2) and third share (A3, B3, C3), concentration values of the first solute (C_A1, C_B1, C_C1), concentration values of the second solute (C_A2, C_B2, C_C2) and concentration values of the third solute (C_A3, C_B3, C_C3);

determine a first mass balance error (Err1), a second mass balance error (Err2) and a third mass balance error (Err3) on the basis of at least one of said concentration values of the first solute (C_A1, C_B1, C_C1), concentration values of the second solute (C_A2, C_B2, C_C2) and concentration values of the third solute (C_A3, C_B3, C_C3), said first mass balance error (Err1) concerning said first solute, said second mass balance error (Err2) concerning said second solute, and said third mass balance error (Err3) concerning said third solute;

determine, for each one of said first solute, second solute and third solute, a clearance value (K1, K2, K3) and/or a sieving coefficient (H1, H2, H3) or an effluent saturation coefficient when each one of said first mass balance error (Err1), second mass balance error (Err2) and third mass balance error (Err3) is comprised between −10% and +10%.

7. The analysis apparatus according to claim 6, wherein each one of said concentration values of the first solute (C_A1, C_B1, C_C1), concentration values of the second solute (C_A2, C_B2, C_C2) and concentration values of the third solute (C_A3, C_B3, C_C3) can be determined in accordance with one or more of the following methods: immunofluorimetric method, colorimetric method, UV method, electrochemical method, immunoturbidimetric method, and potentiometric method.

8. The analysis apparatus according to claim 6, wherein a storage unit comprises said first collection chamber, said second collection chamber and said third collection chamber, said storage unit being removable from said analysis apparatus.

9. A system for acquiring liquid biological samples from an extracorporeal circuit for subjecting a patient to an extracorporeal blood purification treatment, said system comprising a machine for subjecting a patient to an extracorporeal blood purification treatment, an apparatus for acquisition of liquid biological samples according to claim 4, and said extracorporeal circuit, operatively connected to one another.

* * * * *